United States Patent [19]

Schor

[11] 4,357,469

[45] Nov. 2, 1982

[54] CARRIER BASE MATERIAL FOR PROLONGED RELEASE THERAPEUTIC COMPOSITIONS

[75] Inventor: Joseph M. Schor, Locust Valley, N.Y.

[73] Assignee: Forest Laboratories, Inc., New York, N.Y.

[21] Appl. No.: 278,568

[22] Filed: Jun. 29, 1981

Related U.S. Application Data

[60] Continuation-in-part of Ser. No. 127,433, Mar. 3, 1980, abandoned, which is a division of Ser. No. 48,344, Jun. 14, 1979, Pat. No. 4,226,849.

[51] Int. Cl.$^3$ .................. A61K 47/00; C08B 11/20; C08B 11/193; C08L 1/26
[52] U.S. Cl. .................. 536/91; 106/169; 106/171; 106/197 R; 106/197 C; 536/85; 536/87
[58] Field of Search .............. 536/85, 87, 91; 106/169, 171, 197 R, 197 C

[56] References Cited

U.S. PATENT DOCUMENTS 3,590,117  6/1971  Christenson et al. .............. 424/19
3,594,467  7/1971  Christenson et al. .............. 424/19
3,870,790  3/1975  Lowey et al. .............. 424/19
4,226,849  10/1980  Schor .............. 424/19

FOREIGN PATENT DOCUMENTS 1018456  10/1977  Canada .
1171691  11/1969  United Kingdom .
1279214  6/1972  United Kingdom .

*Primary Examiner*—Ronald W. Griffin
*Attorney, Agent, or Firm*—Jacobs & Jacobs

[57] ABSTRACT

A carrier base material adapted to be combined with a therapeutically active medicament and shaped and compressed to form a sustained release therapeutic composition having a long-lasting, slow and regular incremental release of the medicament upon administration, the carrier base material being hydroxypropylmethylcellulose or a mixture of hydroxypropylmethylcellulose and either up to 30% ethylcellulose or 30% sodium carboxymethylcellulose or both, and wherein the carrier base material has been subjected to hydrolysis and oxidation successively or concurrently until the carbonyl content ranges from 0.2–3.0 grams/100 grams, the carboxyl content ranges from 0.60–2.60 grams/100 grams and the moisture content is in the range of 0.5–3.9%.

3 Claims, No Drawings

CARRIER BASE MATERIAL FOR PROLONGED RELEASE THERAPEUTIC COMPOSITIONS

This is a continuation-in-part of U.S. application Ser. No. 127,433, filed Mar. 5, 1980, now abandoned, which, in turn, is a division of application Ser. No. 48,344, filed June 14, 1979 now U.S. Pat. No. 4,226,849.

BACKGROUND OF THE INVENTION

1. Field of Invention

This invention relates to a carrier base material adapted to be combined with a therapeutically active medicament and formed into a solid shaped dosage unit having a long-lasting and regular incremental release of the medicament upon administration. Specifically, this invention relates to a carrier base material, consisting essentially or predominantly of hydroxy-propylmethylcellulose, whose structure has been modified for use in prolonged release therapeutic compositions.

2. Description of the Prior Art

Hydroxypropylmethylcellulose has been used in the preparation of buccal or sublingual products for transmucosally acting medicaments, as described in British Pat. Nos. 1,171,691 and 1,279,214 and U.S. Pat. No. 3,870,790. Hydroxypropylmethylcellulose has been considered to be lacking in the most desirable properties for making compressed long-lasting troches and, as a result, dry skim milk powder combined with guar gum has been substituted (U.S. Pat. No. 3,590,117). Carboxypolymethylene and sodium caseinate have also been used for the same purpose (U.S. Pat. No. 3,594,467).

While it is known that buccal or sublingual lozenges and tablets intended to be swallowed can be made with various active agents and carriers, where steady prolonged medication is required and a regular rate of release is needed with good absorption of medicament, no fully satisfactory carrier has heretofore been produced. Lowey et al. (U.S. Pat. No. 3,870,790) disclosed a process for preparing a long-acting composition consisting of a therapeutic agent and a carrier, wherein the carrier consisting essentially of hydroxypropylmethylcellulose or hydroxypropylmethylcellulose admixed with ethylcellulose, is subjected to controlled humidity for a time sufficient to establish a moisture content of from about 5 to 25% and then mixed with the therapeutic agent. The present invention is directed towards further improvements in carrier bases prepared from hydroxypropylmethylcellulose.

SUMMARY OF THE INVENTION

An object of the present invention is to provide a carrier material for use in the preparation of orally, bucally or sublingually, etc. administered lozenges and tablets as well as suppositories which have a regular and prolonged release pattern for a systemically absorbable medicament or active ingredient incorporated therein.

Another object of the present invention is to provide a chemically modified carrier base having greater stability and reduced water solubility from hydroxypropylmethylcellulose.

It has now been found that this improvement in a carrier base can be achieved by subjecting hydroxypropylmethylcellulose to conditions which promote hydrolysis and oxidation and produce a carrier material characterized by a carbonyl content of at least 0.2 gram/100 grams and a carboxyl content of at least 0.37 gram/100 grams.

DETAILED DESCRIPTION OF THE INVENTION

According to the present invention, it has now been discovered that important advantages and improvements over prior products containing hydroxypropylmethylcellulose, as described in U.S. Pat. Nos. 3,594,467 and 3,870,790 and British Pat. Nos. 1,171,691 and 1,279,214, can be obtained by special treatment thereof under controlled conditions so as to chemically modify the structure as a result of hydrolysis and oxidation, prior to incorporation of active medicament therein, and thus the inherently desirable properties of hydroxypropylmethylcellulose can be taken advantage of in a significantly improved sustained continuous release compressed lozenge, tablet or suppository capable of providing steady therapeutic blood levels. The present invention therefore subjects hydroxypropylmethylcellulose to conditions which promote hydrolysis and oxidation thereby producing a chemically modified carrier material having about the same molecular weight but a unique chemical structure having greater stability, reduced water solubility, less likelihood of impaction as well as being bland and non-irritating. The chemically modified hydroxypropylmethylcellulose carrier material is characterized by a carbonyl content of at least 0.2 gram/100 grams and a carboxyl content of at least 0.37 gram/100 grams. The carbonyl content may range from 0.2 to 3.0 grams/100 grams with a preferred carbonyl content of 0.2-2.0 grams/100 grams. The carboxyl content may range from 0.37 to 2.6 grams/100 grams.

The hydroxypropylmethylcellulose used as the starting material for the present invention is known and commercially available as Methocel E (Dow Chemical Co.), a premium grade used for pharmaceutical products. This cellulose ether has a methoxyl content of 28–30 weight-% which represents a methoxyl degree of substitution of 1.8–2.0 and a hydroxypropoxyl content of 7.5–12 weight-% which represents a molar substitution of 0.20–0.31.

The hydroxypropylmethylcellulose can be optionally mixed with about 0 to 30% by weight of the mixture of ethylcellulose and/or about 0 to 30% of sodium carboxymethylcellulose. Thus, the hydroxypropylmethylcellulose content of the carrier base can range from 40 to 100%. The hydroxypropylmethylcellulose may be processed alone and then mixed in powder form with ethylcellulose and/or sodium carboxymethylcellulose. Alternatively, a mixture of hydroxypropylmethylcellulose with ethylcellulose and/or sodium carboxymethylcellulose is subjected in powder form to the hereinafter described processing steps. After the materials are processed as described, an active ingredient in suitable amount to provide an effective unit dose per lozenge, tablet or suppository is incorporated therein.

The active ingredient can be of any type of medication which acts systemically and can be administered orally to transmit the active medicament into the gastrointestinal tract and into the blood stream in therapeutically effective levels without early excessive peak concentrations, without being inactivated by physiological fluids and without passing unchanged through the body of the patient or subject by being excreted unabsorbed. Alternatively, the active ingredient can be of any type of medication which acts through the buccal tissues of the mouth to transmit the active ingredient directly into the blood stream thus by-passing the gastric and intestinal fluids which often have an adverse inactivating or destructive action on many active ingredients unless they are specially protected against such fluids as by means of an enteric coating or the like. The active ingredient can also be of a type of medication which can be transmitted into the blood circulation through the rectal tissues.

Representative active medicaments include antacids, anti-inflammatory substances, coronary dilators, cerebral dilators, vasodilators, antibacterials, psychotropics, antimanics, stimulants, antihistamines, laxatives, decongestants, vitamins, etc. However, it is to be understood that the invention is applicable to sublingual lozenges, suppositories and compressed tablets, the latter being intended to be swallowed in unit dosage form and which upon ingestion according to a prescribed regimen give slow and regular release of active medicament without an initial dumping of a fixed percentage in the intestinal tract while being protected against normally inactivating gastric fluids.

The chemically modified hydroxypropylmethylcellulose alone or with up to 30% of ethylcellulose by weight and/or with up to 30% of sodium carboxymethylcellulose by weight, forms what is herein called a long-acting slow dissolving carrier of such nature that it has a protective, demulcent and buffering effect in the body and causes the active medicament to exert its optimum therapeutic action immediately and incrementally for up to several hours so that full therapeutic advantage can be taken of the entire or substantially the entire amount of active medicament administered. This unexpectedly high degree of efficiency is a particular advantage of the invention and minimizes side effects of the medication.

The chemically modified hydroxypropylmethylcellulose of the present invention is prepared by exposing the cellulose ether successively or concurrently to hydrolyzing and oxidizing conditions.

The hydrolysis may be carried out by placing the Methocel in a humidifying chamber and exposing it to high humidity conditions at room or elevated temperatures. Typically, when the humidity of the chamber reaches at least 85%, the material is maintained under this humidity for at least 12 hours. Alternatively, the Methocel is mixed with water, e.g. 50-100% of its weight of water, and heated at a temperature of 30-100° C. for at least 12 hours. The temperature may be varied over a wide range. The optimum time, temperature and water content of the reaction mixture are determined by the available equipment.

After the hydrolysis of the Methocel has been carried out, the product is subjected to oxidation. In one method, the product is heated in an oven at about 30° to 50° C., while a stream of oxygen or forced air is passed over the polymer. In another method, the hydrolyzed Methocel is placed in a vertical tube or tower and air or oxygen which has been mixed with water or steam or has been passed through water at room or elevated temperature and then reheated, if necessary, to a temperature of at least 30° C., is passed upwards through the Methocel. If necessary, the tower is heated to maintain the temperature of about 30° to 50° C. The passage of air is continued for at least 5 hours and until chemical analysis indicates that the desired carbonyl and carboxyl contents have been obtained.

In an alternative method, the hydrolysis and oxidation reactions may be carried out in one step by subjecting the hydroxypropylmethylcellulose to treatment with air or oxygen containing a sufficient amount of water, at an elevated temperature, e.g. in a fluid bed process.

The moisture content of the chemically modified hydroxypropylmethylcellulose is generally in the range of 0.5-10%. If necessary, it may be brought to this level by additional forced air heating, by the passage of heated air over or through the material or by heating in vacuo. The attainment of a moisture content in the desired range without oxidation yields an unsatisfactory product. Thus, if Methocel E-50 is subjected to high humidity for an extended period of time and the wet and/or hydrolyzed Methocel then undergoes drying in vacuo in the absence of air, the carboxyl content of the product is below the desired level and the product does not possess the desirable or acceptable performance characteristics when used as a carrier in the preparation of a sustained release therapeutic composition.

The carbonyl content of the polymer is determined by reaction with hydroxylamine hydrochloride in 0.1 N NaOH, followed by titration of the residual base with 0.1 N HCl. Thus, about 1 gram of polymer sample is weighed into a 500 ml Erlenmeyer flask containing a magnetic stirring bar, and 50 ml distilled water is added. After the mixture is stirred for 30 minutes at room temperature, 25 ml of a solution of hydroxylamine hydrochloride (50 grams hydroxylamine hydrochloride dissolved in 120 ml 1 N NaOH and diluted to 1000 ml) is added. The mixture is heated to 50° C. and stirred for at least 2 hours and until all of the sample has dissolved. The solution is cooled to room temperature under cold tap water and titrated potentiometrically with 0.1 N HCl to pH 3.2.

The carboxyl content of the polymer is determined by reaction with excess 0.1 N NaOH, followed by titration of the residual base with 0.1 N HCl. Thus, about 1 gram of polymer sample is weighed into a 250 ml Erlenmeyer flask containing a magnetic stirrer and 50 ml distilled water is added. After the mixture is stirred for 30 minutes at room temperature, 25 ml of 0.1 N NaOH is added and the mixture is stirred at room temperature for at least 2 hours and until all of the sample has dissolved. The solution is titrated with 0.1 N HCl using phenolphthalein as indicator.

The untreated hydroxypropylmethylcellulose generally has a carbonyl content below 0.9 gram/100 grams and a carboxyl content below 0.37 gram/100 grams. After hydrolysis and oxidation, the carbonyl content is in the range of 0.2 to 3.0 grams/100 grams and the carboxyl content is in the range of 0.37 to 2.6 grams/100 grams.

| Moisture content, weight-% | Carbonyl content, g/100 g | Carboxyl content, g/100 g |
|---|---|---|
| 4.0-10 | 0.2-3.0 | 0.37-0.59 |
| 0.5-3.9 | 0.2-3.0 | 0.60-2.60 |

When the required carbonyl and carboxyl contents are attained, the chemically modified hydroxypropylmethylcellulose is passed through a No. 2 stainless steel screen employing a Fitzpatrick Comminuter having its knives directed forward and operating at medium speed.

The hydrolysis-oxidation treatment may be applied to a mixture of hydroxypropylmethylcellulose and up to 30% ethylcellulose and/or up to 30% sodium carboxymethylcellulose. In this case, after the moisture content has been reduced to the 0.5-10% range, the comminution step may be omitted since the material is free flowing and powdery. The moisture content of the carrier plays a role in the preparation of shaped carrier-medicament compositions and influences the integrity of the product.

By way of example, in making up tablets containing an orally administrable systemically absorbable active component such as one of the heretofore mentioned medicaments, the treated oral carrier material is thoroughly intermixed with the medicament which is also in powdered or granular form and any other needed ingredients which are conventional in tablet making such as magnesium stearate, lactose, starch and, in general, binders, fillers, disintegrating agents, and the like. The complete mixture, in an amount sufficient to make a uniform batch of tablets, such as 50,000, of which each contains an effective amount of active medicament, is then subjected to tableting in conventional tableting machines but at, for example, compression pressures of 4 to 15 kg/in.$^2$ and because of the use of the specially processed carrier material in the production of the tablets, a product is obtained which has a desired set of properties such as predetermined prolonged action and a regular delayed release pattern so that the medicinal agent or active ingredient is available over a period of 1-12 hours depending on the precise tablet size and hardness and the particular carrier mixture. In this way it is possible to produce sustained or slow continuous release tablets in relatively simple and economical manner on a commercial scale as contrasted with the more elaborate and more complex materials and procedures heretofore employed or proposed.

Procedures for preparing the chemically modified hydroxypropylmethylcellulose or mixtures thereof with ethylcellulose or sodium carboxymethylcellulose are illustrated by the following examples which are non-limiting and can be modified so as to utilize other equipment or procedures for hydrolysis and/or oxidation which are well known to those skilled in the art.

EXAMPLE NO. 1

Hydroxypropylmethylcellulose (Methocel E-50) or a mixture of hydroxypropylmethylcellulose with ethylcellulose and/or sodium carboxymethylcellulose is introduced into a heating chamber provided with an exhaust which is at that time in closed or shut position and which chamber is provided with a heating unit and a forced air blower which is inoperative at this stage of the procedure in that the heat and forced air are only applied at a subsequent stage. The carrier material to be processed is placed in thin layers (not more than ¼" thick) on trays of the chamber which are lined with heat-resistance parchment paper and the trays are placed on racks in the oven chamber using only alternate shelves thereby providing adequate spacing between the layers of carrier material being treated. There is then placed within the oven chamber a humidifier equipped with a humidistat which is preset to maintain humidity in the oven chamber at about 85%, the humidifier being filled with sufficient distilled or deionized water to last for 24 to 36 hours.

The humidifier employed is Arvin Model 50 H 42 (Sears Roebuck) — 10 gallon capacity having low and high air speeds and the humidistat is provided with nine settings for moisture control. In the present example the humidistat is set to position 7 which maintains 85-90% humidity in the oven chamber per 250 cubic feet of airflow and a temperature of approximately 75° F. (24° C.).

The humidifier is activated and the heating chamber is closed. The process is allowed to proceed under 85-90% humidity for 24 hours. The humidifier is then removed from the heating chamber, the exhaust aperture opened by manipulation of the valve, and the forced air blower is activated so as to apply heat at a temperature of 110°-120° F. (43°-49° C.). At the end of 12 hours the carbonyl and carboxyl contents of the treated material are checked by removing and analyzing a sample. The moisture content is 5.0%. The carbonyl and carboxyl contents of the treated material are 1.34 and 0.54 grams/100 grams, respectively, whereas the untreated cellulose ether has carbonyl and carboxyl contents of 0.56 and 0.33 grams/100 grams, respectively.

The treated material is removed from the oven and passed through a No. 2 stainless steel screen employing a Fitzpatrick Comminuter at medium speed.

EXAMPLE NO. 2

A 1000 gram batch of Methocel E-50 was mixed with 1000 grams of water in a Waring Blender. The mixture was placed in a glass jar which was closed with a canning lid containing a self-sealing rubber gasket. The jar was kept in an oven at 90° C. for 24 hours to effect hydrolysis.

The hydrolyzed Methocel was transferred to a vertical cylinder which was wrapped with heating tape so as to maintain a bed temperature of about 50° C. Air was pumped into a flask containing water at 60° C., then through copper coils immersed in a 50° C. water bath and then into the bed of polymer. The hot, wet air entered at the bottom of the bed of polymer, and by means of a manifold which permitted the air to enter the polymer bed at four points through perforated tubes, passed upward through the bed as a finely dispersed gas stream. The oxidation was carried out for 24 hours at 50° C.

Samples of the untreated, hydrolyzed and oxidized Methocel E-50 were dried in vacuo to constant weight and subjected to analysis. The results were as follows:

| Methocel E-50 | Carbonyl content, g/100 g | Carboxyl content, g/100 g |
|---|---|---|
| Untreated | 0.80 | 0.34 |
| Hydrolyzed | 1.95 | 0.40 |
| Oxidized | 1.59 | 0.89 |

The viscosities of 2% aqueous solutions of the untreated, hydrolyzed and oxidized materials at 25° C. were essentially the same, indicating that the hydrolysis and oxidation reactions did not result in chain cleavage and there was no reduction in molecular weight of the cellulose ether.

Compositions containing the chemically modified hydroxypropylmethylcellulose are illustrated in non-limiting Examples No. 3-16, wherein "Synchron Carrier" refers to the carrier base prepared by the process described in Example No. 1 and having the carbonyl and carboxyl contents indicated therein.

EXAMPLE NO. 3

Demulcent and Adsorbent

A demulcent and adsorbent lozenge was prepared from the following ingredients in the following relative proportions.

|   | Ingredients | mg/tablet |
|---|---|---|
| 1 | Synchron Carrier | 232 |
| 2 | Gastric mucin | 25 |
| 3 | Aluminum hydroxide gel dried granular | 250 |
| 4 | Magnesium trisilicate granular | 250 |
| 5 | Methyl paraben U.S.P. | 0.8 |
| 6 | Propyl paraben U.S.P. | 0.08 |
| 7 | Felcofix cherry flavor No. 1265 | 16 |
| 8 | Syloid 244 (Silica aerogel) | 5 |
| 9 | Carbowax 6000W | 6.81 |
| 10 | Stearic acid | 8.0 |

Using the foregoing ingredients, a batch weighing 793.69 g was prepared by weighing out ingredients 1–4, screening ingredients 5–10 and mixing and blending all ingredients for 20 minutes following which they were subjected to compression in a tableting machine having a ½" die size and a ½" punch to make tablets with an average weight of 0.794 g and a thickness of 0.210"±0.01". The hardness of the tablet was 11–13 kg/square inch.

EXAMPLE NO. 4

|   | Analgesic Ingredients | mg/tablet |
|---|---|---|
| 1 | Aspirin powder U.S.P. | 525.0 |
| 2 | Synchron Carrier | 325.5 |
| 3 | Glycine | 45.0 |
| 4 | Syloid 244 (Silica aerogel) | 4.5 |

Ingredients 1, 2 and 3 are mixed in a bowl into which ingredient 4 is added after screening and the whole blended for 20 minutes and compressed in the manner described in Example No. 3. Each tablet weighed 0.9 g.

EXAMPLE NO. 5

|   | Antihistamine Ingredients | mg/tablet |
|---|---|---|
| 1 | Chlorpheniramine maleate U.S.P. | 12.60 |
| 2 | Synchron Carrier | 509.20 |
| 3 | Methyl paraben U.S.P. | 0.52 |
| 4 | Propyl paraben U.S.P. | 0.06 |
| 5 | Syloid 244 (Silica aerogel) | 2.63 |

Ingredient 2 was placed in a suitable bowl or container and ingredients 1, 3, 4 and 5 were weighed out and added after screening and the whole blended for 20 minutes following which the compression into tablets took place on a tableting machine using a die size of 7/16" with a punch of 7/16" to obtain a tablet thickness of 0.250"±0.01" with a tablet hardness of 11–13 kg/square inch. Each tablet weighed 0.525 g.

EXAMPLE NO. 6

|   | Appetite Satient Ingredients | mg/tablet |
|---|---|---|
| 1 | Synchron Carrier | 60.0 |
| 2 | Benzocaine | 9.9 |
| 3 | Saccharin | 0.3 |
| 4 | Felcofix peppermint | 1.5 |
| 5 | Felcofix cherry flavor No. 1265 | 2.5 |
| 6 | Carbowax 6000W | 0.4 |
| 7 | Syloid 244 (Silica aerogel) | 0.4 |
| 8 | Methyl paraben U.S.P. | 0.075 |
| 9 | Propyl paraben U.S.P. | 0.0075 |

Ingredient 1 was placed in a stainless steel bowl as in the previous examples and ingredients 2–9 were also weighed out and screened and all ingredients thoroughly mixed and blended in a bowl for 20 minutes following which they were compressed into tablets on a tableting machine having a die size of 7/32" and a punch of 7/32" to form tablets having a thickness of 0.110" and a hardness of 7–10 kg/square inch. Each tablet weighed 0.075 g.

EXAMPLE NO. 7

|   | Laxative Ingredients | mg/tablet |
|---|---|---|
| 1 | Phenolphthalein U.S.P. | 33.00 |
| 2 | Synchron Carrier | 513.64 |
| 3 | Methyl paraben U.S.P. | 0.55 |
| 4 | Propyl paraben U.S.P. | 0.06 |
| 5 | Syloid 244 (Silica aerogel) | 2.75 |

Ingredients 1 and 2 were placed in a stainless steel bowl to which after screening were added ingredients 3, 4 and 5 and the whole blended for 20 minutes and compressed as in Example No. 5. The tablet thickness was 0.250"±0.01" and the hardness was 10 kg/square inch. Each tablet weighed 0.55 g.

EXAMPLE NO. 8

|   | Laxative Ingredients | mg/tablet |
|---|---|---|
| 1 | Phenolphthalein U.S.P. | 66.0 |
| 2 | Synchron Carrier | 480.64 |
| 3 | Methyl paraben U.S.P. | 0.55 |
| 4 | Propyl paraben U.S.P. | 0.06 |
| 5 | Syloid 244 (Silica aerogel) | 2.75 |

The same procedure was followed as in Example No. 7 with the same results.

EXAMPLE NO. 9

|   | Breath Wafers Ingredients | mg/tablet |
|---|---|---|
| 1 | Synchron Carrier | 629.9 |
| 2 | Sorbitol | 37.5 |
| 3 | Mannitol | 37.5 |
| 4 | Sodium bicarbonate U.S.P. granular | 15.0 |
| 5 | Stearic acid | 15.0 |
| 6 | Syloid 244 (Silica aerogel) | 7.5 |
| 7 | Oil of peppermint U.S.P. | 3.8 |
| 8 | Oil of wintergreen U.S.P. | 3.8 |

Ingredients 1–5 were placed in a stainless steel bowl, ingredients 7 and 8 were adsorbed on ingredient 6 and screened and added to the stainless steel bowl. All ingredients were mixed and blended for 20 minutes and compressed as previously described except that the tablets were in wafer form with a thickness of 0.175"±0.01" with a hardness of 8–10 kg/square inch. Each tablet weighed 0.75 g.

EXAMPLE NO. 10

| | Decongestant | |
|---|---|---|
| | Ingredients | mg/tablet |
| 1 | Synchron Carrier | 728.5 |
| 2 | Sorbitol | 42.5 |
| 3 | Mannitol | 42.5 |
| 4 | Stearic acid | 17.2 |
| 5 | Menthol | 4.3 |
| 6 | Oil of Eucalyptol | 2.1 |
| 7 | Camphor | 4.3 |
| 8 | Syloid 244 (Silica aerogel) | 8.6 |

Ingredients 1–4 were screened and placed in a stainless steel bowl, ingredients 5, 6 and 7 were triturated until they became liquid and then adsorbed on ingredients 8. The mixture was screened into the other ingredients which had already been placed into the stainless steel bowl and blended and compressed as previously described. The tablets had a thickness of 0.200"±0.01" and a hardness of 8–10 kg/square inch. Each tablet weighed 0.85 g.

EXAMPLE NO. 11

| | Vitamin | |
|---|---|---|
| | Ingredients | mg/tablet |
| 1 | Ascorbic acid U.S.P. powder | 105 |
| 2 | Synchron Carrier | 691 |
| 3 | Syloid 244 (Silica aerogel) | 4 |

Ingredients 1 and 2 were weighed out as in the preceding examples and placed into a stainless steel bowl into which ingredient 3 was added after screening and the whole blended for 20 minutes and compressed as previously described. The tablets had a thickness of 0.210"±0.01" and a hardness of 11–13 kg/square inch. Each tablet weighed 0.8 g.

In Examples No. 12–16 the quantities shown are utilized in the preparation of 50,000 dosage units and the blending and tableting are carried out as previously described.

EXAMPLE NO. 12

| Vasodilator | |
|---|---|
| Nitroglycerin | 325 g. |
| Beta Lactose | 2,975 g. |
| Syloid No. 244 | 50 g. |
| Cherry flavor | 100 g. |
| Synchron Carrier | 23,750 g. |

EXAMPLE NO. 13

| Anti-inflammatory | |
|---|---|
| Prednisolone | 250 g. |
| Synchron Carrier | 9,465 g. |
| Syloid No. 244 | 50 g. |
| Cherry flavor | 100 g. |

EXAMPLE NO. 14

| Anti-Manic depressive | |
|---|---|
| Lithium Carbonate | 15,000 g. |
| Synchron Carrier | 19,880 g. |
| Syloid No. 244 | 10 g. |
| Cherry flavor | 15 g. |

EXAMPLE NO. 15

| Antacid | |
|---|---|
| Aluminum Hydroxide Gel | 12,500 g. |
| Magnesium Glycinate | 12,500 g. |
| Gastric Mucin | 5,000 g. |
| Carbowax 6000 W | 34.5 g. |
| Synchron Carrier | 12,000 g. |
| Syloid No. 244 | 250 g. |
| Cherry flavor | 500 g. |

EXAMPLE NO. 16

| Antibiotic | |
|---|---|
| Ampicillin | 12,500 g. |
| Synchron Carrier | 2,500 g. |
| Syloid No. 244 | 30 g. |
| Cherry flavor | 25 g. |

In our earlier U.S. Pat. No. 3,870,790 it was disclosed that the use of a premoisturized hydroxypropylmethylcellulose powder having a moisture content of from about 5 to about 25% in the preparation of a compressed solid dosage unit containing an active therapeutic ingredient, gave sustained release compositions. The release was controlled by the increased compression or higher degree of compression pressure permitted by the presence of the indicated amount of moisture.

In the present invention, it has been found that a significantly greater control of the release pattern is achieved by a chemical modification which results in an increase in the carboxyl functionality in the hydroxypropylmethylcellulose molecule. Although the actual mechanism is not known, it may be speculated that the slower release rate arises from a decreased rate of swelling or a lower water solubility resulting from a hydrogen-bonding interaction between the carboxyl and the carbonyl and/or hydroxyl groups in the hydroxypropylmethylcellulose which has been subjected to both hydrolysis and oxidation.

In contrast to the disclosure of U.S. Pat. No. 3,870,790 it has now been found that moisture contents as low as 0.5% can be present during the preparation of tablets and other compressed solid shapes. The amount of moisture present influences the amount of pressure necessary to prepare the shaped objects and the integrity thereof but plays a minor role as compared to the chemical structure in the rate of release of medicaments from the chemically modified hydroxypropylmethylcellulose. Similarly, while the release pattern is governed at least in part by the size of the tablet or other shaped object as well as by the degree of compression, the chemical structure of the hydroxypropylmethylcellulose which has been subjected to chemical modification superimposes its effect and is the dominant factor in the control of the release rate.

It should be noted that the improvement in release characteristics has been attained by treating the same hydroxypropylmethylcellulose used earlier. Thus, while U.S. Pat. No. 3,870,790 refers to Methocel HG 60 and the present invention refers to Methocel E-50, these are the same materials, the manufacturer having changed the designation in the interim.

The release pattern of active medicament from the new carrier can be controlled according to the particular medication and its intended therapeutic effect. For a sublingual lozenge or tablet the release pattern may be varied from about ¼ hour to 4 hours. For orally administered tablets, the rate of release may be 4–8 hours or 8–10 hours, as desired, and this has been confirmed by X-rays with barium sulfate to show the motility and disintegration of the tablet as it proceeds down the intestinal tract. For vaginal and rectal suppositories the release pattern ranges from 12 to 36 hours, although, of course, it can be less where indicated. Predetermined release patterns of unusually reliable and constant characteristics can be secured. This is often very important medically, especially when treating patients having coronary diseases, such as angina pectoris as with nitroglycerin, or related problems of circulatory disorders or abnormal blood pressure conditions or psychotropic/manic depressive schizophrenia. The invention is particularly important also in treating such conditions as ulcerated tissue or mucous lesions and other conditions arising from local hyperacidity or metabolic dysfunction in the physiological system. The invention is therefore of very versatile and adaptable nature giving it a wide range of application and end use.

The foregoing is exemplary of compositions and products responding to the present invention, but it is to be understood that they are illustrative and not limitative since many active ingredients of various types can be employed in the new longlasting carrier so long as they are absorbable into blood or tissue from the general intestinal tract, etc. The invention is also intended to cover other dosage forms or forms for application of sustained release ingredients such as vaginal and rectal suppositories. The lozenges and tablets particularly act on oral, oropharyngeal and pharyngeal regions. The total dosage is governed by usual medical considerations or physicians' directions and when sufficiently large doses of active medicament are incorporated in the unit dosage form, systemic as well as local action is obtained to overcome or control the pathological condition or disorder being treated.

The presence of a stabilizing agent in the oral carrier tends to prevent undesired changes in the carbonyl and carboxyl contents during shipping and storage. A reducing agent such as ascorbyl stearate or palmitate or sodium metabisulfite may be added to the carrier material to inhibit oxidation. The stabilizer or reducing agent is usually added after the hydroxypropylmethylcellulose has been subjected to the hydrolysisoxidation treatment, in a concentration of 0.1–1.0% of the weight of the carrier material.

In evaluating drugs incorporated in the oral carrier system or base of the present invention, it is important to understand the factors influencing the absorption and therapeutic effectiveness of drug products in compositions responding hereto. Under usual circumstances, disintegration of a tablet into small particles in the gastrointestinal fluids speeds dissolution because of much increased surface area of the drug. Consequently, absorption is more rapid and the duration of therapeutic action depends primarily upon the rate of absorption. The rate and extent of drug absorption thus can influence both the duration of action and the efficacy of drug therapy. It follows that the faster the absorption, the earlier peak level of drug is reached but if absorption is too slow, the concentration of drug in blood tissues may never reach therapeutic levels. Subsequent to absorption, there is a drop in concentration that depends in large part upon elimination and/or metabolism.

Drugs embedded in the present "Synchron" Carrier System, as I term the carrier base, are intended to attain and maintain a steady concentration of drug in blood or tissues. One objective in using these preparations is to reduce the dosage frequency, to make therapy simple and convenient, and to improve compliance by the patient. In addition, by maintaining a reasonably constant plasma concentration of drug, excessive or premature peaking is avoided and side effects, which may be associated with peak concentrations of drug, would be lessened. In addition, a more uniform concentration of drug in blood and tissues is much more likely to be paralleled by a more uniform pharmacologic effect and response. With disolution being the main rate-limiting step in drug absorption, the rate of solution of the drug from the dosage form into the surrounding fluids at the absorption site is controlled by the chemical changes induced during production of the "Synchron" Carrier System. With the "Synchron" Carrier System the drug can further be released to a specific site at a uniform rate independently of th pH environment, resulting in steady concentrations of the drug in tissues. Drugs incorporated into the "Synchron" Carrier System vehicle are prone to be absorbed completely, but more slowly, and are formulated to maintain the therapeutic effective level of the particular drug and to produce a prolonged response and a diminished rate of unassimilated drug elimination.

The absorption data may be determined and expressed as the cumulative percentage of the dose absorbed plotted against time, or analyzed further to derive information as to the kinetics of the absorption process. Usually the total body clearance of a drug is fixed. Then the total area under the plasma concentration-time curve is proportional to the dose absorbed and independent of the rate of absorption. Area analysis forms the basis for estimation and comparison of the extent of absorption when the same dose is given in different dosage forms or by different routes of administration, or in different carrier systems. The "Synchron" Carrier System has the added advantage compared to other available prolonged-release vehicles employed in dosage forms insofar as it will not release the drug in a dumping action and prevents the potential hazard of over-dosage if all the drug is released at one time and is rapidly absorbed. The method for determining sustaining dose with the present carrier system may be expressed by the formula:

$$D \times 0.693 \times SV/L_{\frac{1}{2}},$$

wherein D is the normal therapeutic dose, SV is the number of hours desired to extend the duration of action, and $L_{\frac{1}{2}}$ is the drug's half-life. The primary difference between the use of my "Synchron" Carrier System and other sustained-release vehicles is that the dissolution of the vehicle is not dependent upon th pH or the enzymatic activity of the intestinal fluids. Site action predetermination is possible via the concentration of the vehicle in the dosage form.

What is claimed is:

1. A carrier base material adapted to be combined with a therapeutically active medicament and shaped and compressed to form a sustained release therapeutic composition having a longlasting, slow and regular incremental release of the medicament upon administration, the carrier base material being hydroxypropylmethylcellulose or a mixture of hydroxypropylmethylcellulose and up to 30% ethylcellulose or 30% sodium carboxymethylcellulose or both, and wherein the carrier base material has been subjected to hydrolysis and oxidation successively or concurrently until the carbonyl content ranges from 0.2–3.0 grams/100 grams, the carboxyl content ranges from 0.60–2.60 grams/100 grams and the moisture content is in the range of 0.5–3.9%.

2. A carrier base material according to claim 1 in which has been incorporated 0.1–1.0%, based on the weight of the carrier base, of a reducing agent which prevents undesired further oxidation.

3. A carrier base material according to claim 2 wherein the reducing agent is selected from the group consisting of ascorbyl stearate, ascorbyl palmitate and sodium metabisulfite.

* * * * *